United States Patent [19]

Ishimi

[11] 4,001,316
[45] Jan. 4, 1977

[54] METHOD FOR MANUFACTURE OF METHACRYLIC ACID

[75] Inventor: Kazuo Ishimi, Takasaki, Japan

[73] Assignee: Nippon Kayaku Kabushiki Kaisha, Tokyo, Japan

[22] Filed: Mar. 17, 1975

[21] Appl. No.: 558,939

Related U.S. Application Data

[62] Division of Ser. No. 481,255, June 20, 1974, Pat. No. 3,956,182.

[30] Foreign Application Priority Data

June 30, 1973 Japan .............................. 48-74014
Dec. 14, 1973 Japan .............................. 48-138691
Feb. 21, 1974 Japan .............................. 49-19933

[52] U.S. Cl. .......................... 260/530 N; 252/435; 252/437; 260/530 R
[51] Int. Cl.$^2$ ........................................ C07C 51/32
[58] Field of Search ............... 260/530 N; 252/435, 252/437

[56] References Cited

UNITED STATES PATENTS 3,875,220    4/1975    White et al. .................. 260/530 N

*Primary Examiner*—Vivian Garner
*Attorney, Agent, or Firm*—Lane, Aitken, Dunner & Ziems

[57] ABSTRACT

The invention relates to the vapor phase oxidation of methacrolein to methacrylic acid with molecular oxygen or a molecular oxygen-containing gas and a catalyst having the following composition:

$Mo_aP_bSb_cZn_dX_eO_f(NH_4)_g$ wherein X is at least one of Cr, W, Fe, Co, Ni, Cu, Sn, Mn, V and Bi. The subscripts $a, b, c, d, e, f$ and $g$ are as defined below.

6 Claims, No Drawings

METHOD FOR MANUFACTURE OF METHACRYLIC ACID

This is a division of application Ser. No. 481,255 filed June 20, 1974, now U.S. Pat. No. 3,956,182.

DETAILED DESCRIPTION OF THE INVENTION

This invention relates to a method for manufacturing methacrylic acid by oxidizing methacrolein utilizing an oxidation catalyst.

More specifically, this invention relates to a method for manufacturing methacrylic acid utilizing a catalyst of the following composition to produce methacrylic acid by oxidizing methacrolein with molecular oxygen or a molecular oxygen-containing gas:

$$Mo_a P_b Sb_c Zn_d X_e O_f (NH_4)_g$$

wherein, X denotes at least one element selected from the group consisting of chromium, tungsten, iron, cobalt, nickel, copper, tin, manganese, vanadium and bismuth, the subscripts $a$, $b$, $c$, $d$, $e$ and $f$ respectively denote the numbers of molybdenum, phosphorus, antimony, zinc, X and oxygen atoms, the subscript $g$ denotes the number of ammonium groups and, wherein $a$ is fixed at 12, $b$ assumes a value of 0.8 to 6, $c$ a value of 0.1 to 7, $d$ a value up to 4 but not including 0, $e$ a value of 0 to 6 and $g$ a value of 0 to 3.5 and $f$ a value normally falling within the range from 38 to 81 and automatically determined in accordance with the valence of the other atoms involved.

To date, a good number of catalysts have been suggested for use in the synthesis of unsaturated carboxylic acids by oxidizing unsaturated aldehydes such as acrolein and methacrolein.

The specification of U.S. Pat. No. 2,881,212, for example, discloses a phosphorus-molybdenum type catalyst. However, the methacrylic acid-producing activity of this catalyst is low, giving a yield of methacrylic acid of only 6.6%. In the abstract in the Japanese Patent Gazette for Patent Publication No. 23367/1971, a phosphorus-molybdenum-chromium type catalyst is disclosed. With this catalyst, a 95.1% methacrolein conversion, 60.1% methacrylic acid selectivity and only a 57.2% methacrylic acid yield are obtained at a reaction temperature of 380° C. From the commercial standpoint it is desirable to develop an oxidation catalyst which provides high activity and high selectivity and yield at an appreciably lower temperature.

The catalyst of this invention described above manifests a new form of catalytic activity during the process of methacrolein oxidation and exhibits high activity at low temperatures which constitutes a merit if important commercial significance producing methacrylic acid with high selectivity. Further, this catalyst enjoys a long active life.

In the reaction effected by using the catalyst of this invention, the conversion of methacrolein is high even at low reaction temperatures and, even with such high methacrolein conversion, the quantities of carbon dioxide and carbon monoxide formed as complete oxidation products of methacrolein are extremely small. Also the amount of heat generated during the course of the reaction is consequently decreased, the temperature within the catalyst bed is uniform, and the occurrence of acetic acid, acrylic acid, acetone, etc. as secondary reaction products is repressed and thus the subsequent refining process becomes extremely easy. The fact that the reaction proceeds at low temperatures and the amount of heat generated is small means that the reaction is easy to control.

The composition of the catalyst of the present invention desirably satisfies the following numerical relationship:

$a:b:c:d:e:f:g = 12:1-5:0.3-6:$a value up to 3 but not including 0:0.1-4:39-71:1-3.5

The catalyst most desirable is one having a composition which satisfies the following numerical relationship:

$a:b:c:d:e:f:g = 12:1.5-4:0.5-4:$a value up to 2 but not including 0:0.5-3:42-63:1.5-3

Although the structure of the catalyst of the present invention is not definitely known, it is believed to contain a complex of heteropolyacids in addition to the oxides of the respective metals.

In the method of this invention, methacrolein and molecular oxygen or a molecular oxygen-containing gas are used as reactants. Generally, air is used as the molecular oxygen-containing gas.

The gaseous raw feed may contain inert gases such as nitrogen, carbon dioxide, etc.

A desirable molar ratio of methacrolein to oxygen in the raw food gas is 1:0.5–15, preferably 1:1–7.

It is also desirable that the raw feed gas contain water. Generally, the raw feed gas permits the presence of steam corresponding to a 1 to 20 molar ratio, which is based upon the methacrolein content of the feed gas.

In preparing the catalyst of this invention, any of the generally known methods available for the production of this type of catalyst can be applied. For example, the catalyst can be prepared by mixing the starting materials of the component elements, where necessary in conjunction with aqueous ammonia, drying the resultant mixture and calcining the dried mixture in the range of 300° to 500° C, and preferably in the range of 350° to 430° C.

In preparing the catalyst in this invention, the starting materials for the component elements can be in various forms. They may be oxides, the metals themselves, metal salts and acid salts of the respective component elements.

Examples of the starting materials for molybdenum include; molybdic acid, ammonium molybdate, molybdenum trioxide, phosphomolybdic acid, zinc molybdate, manganese molybdate, iron molybdate, cobalt molybdate and nickel molybdate. Examples of the starting materials for phosphorus are; orthophosphoric acid, pyrophosphoric acid, ammonium phosphate, phosphomolybdic acid, zinc phosphate, phosphotungstic acid, manganese phosphate, cobalt phosphate, nickel phosphate and tin phosphate. Examples of the starting materials for antimony include: antimony trioxide, antimony pentoxide and antimony hydroxide. The starting materials for zinc include; zinc phosphate, zinc tungstate, zinc chromate, zinc molybdate, zinc sulfate and zinc nitrate. The starting materials for chromium include chromium phosphate, zinc chromate, chromium oxide, chromic acid, ammonium chromate and copper chromate. The starting materials for tungsten include; zinc tungstate, tungstic acid, phosphotungstic acid and ammonium paratungstate. And the starting materials for iron; cobalt, nickel, copper, manganese, tin and bismuth include salts such as phosphates or molybdates ammonium metavanadate is one example of a starting material for vanadium.

The catalyst in the present invention produces methacrylic acid in high yields even without the use of a carrier. To increase the mechanical strength of the catalyst or increase the heat resistance of the catalyst, the catalyst may be formed with a suitable carrier. The carrier may be a substance such as powdered silicon carbide, powdered aluminum, α-alumina and cerite which are chemically inert to methacrolein and methacrylic acid.

In practicing the method of this invention, the reaction is desirably conducted at temperatures falling within the range of 230° to 370° C.

The supply rate at which the raw feed gas is introduced is desirably within the range of 100 to 3000 liters of gas/liter of catalyst per hour, preferably from 250 to 1800 liters of gas/liter of catalyst per hour in terms of space velocity. The optimum reaction conditions are selected with due consideration to such factors as the percentage composition of the catalyst, the reaction temperature and the carrier ratio of the catalyst.

The reaction can be carried out under an increased or decreased pressure. Generally, however, pressure in the neighborhood of atmospheric pressure is suitable.

The catalyst of this invention can be used in the form of a fixed bed, a fluidized bed or a moving bed.

The values of methacrolein conversion, methacrylic acid selectivity, methacrylic acid yield and space velocity (SV) as indicated in the examples to follow have been calculated in accordance with the following definitions:

Conversion of methacrolein (%)

$$= \frac{\text{Number of mols of reacted methacrolein}}{\text{Number of mols of supplied methacrolein}} \times 100$$

Selectivity of methacrylic acid (%)

$$= \frac{\text{Number of mols of formed methacrylic acid}}{\text{Number of mols of reacted methacrolein}} \times 100$$

Yield of methacrylic acid (%)

$$= \frac{\text{Number of mols of formed methacrylic acid}}{\text{Number of mols of supplied methacrolein}} \times 100$$

space velocity (SV)

$$= \frac{\text{Flow volume of raw feed gas (computed as NTP) (liter of gas/hr)}}{\text{Volume of packed catalyst (liters of catalyst)}}$$

The values of the ratios of acetic acid formation, carbon dioxide formation and carbon monoxide formation have been calculated in accordance with the following definitions:

Ratio of acetic acid formation (%)

$$= \frac{\text{Number of mols of formed acetic acid}}{\text{Number of mols of supplied methacrolein}} \times \tfrac{1}{2} \times 100$$

Ratio of carbon dioxide formation (%)

$$= \frac{\text{Number of mols of formed carbon dioxide}}{\text{Number of mols of supplied methacrolein}} \times \tfrac{1}{4} \times 100$$

Ratio of carbon monoxide formation (%)

$$= \frac{\text{Number of mols of formed carbon monoxide}}{\text{Number of mols of supplied methacrolein}} \times \tfrac{1}{4} \times 100$$

EXAMPLE 1

In 200 ml of deionized water, 56.1 g of phosphomolybdic acid was dissolved. 3.9 g of zinc chromate was added thereto and the solution was heated to and kept at about 60° C until the solids had uniformly dissolved. The addition of 12.5 g of antimony trioxide converted the resulting orange transparent liquid into a yellow suspension. The suspension, with 5.0 g of ammonium phosphate and 15 ml of aqueous 28% ammonia solution added thereto, was evaporated to a dry state with vigorous agitation. The cakey substance consequently formed was dried overnight at about 120° to 130° C, crushed to 6 to 10 mesh, packed in a quartz tube having a 25 mm inside diameter and a length of 50 cm and then calcined 405° C for 8 hours under a continuous supply of air at the rate of 6 to 8 liters/hour. The catalyst thus formed had the following composition:

$Mo_{12}P_{2.8}Sb_{3.6}Zn_{0.82}Cr_{0.82}O_{51}(NH_4)_{2.6}$ 20 ml of this catalyst was packed in a reaction tube having an inside diameter of 20 mm and made of Pyrex glass, and a raw feed gas composed of methacrolein, oxygen, steam and nitrogen in the molar ratio of 1:4.1:10.9:15.5 was passed through the packed tube at a 1000 hr$^{-1}$ space velocity (SV) and at a 280° C reaction temperature to effect the oxidation reaction. The results obtained in the constant phase of this reaction were 90.9% methacrolein conversion, 73.8% methacrylic acid selectivity, 67.1% methacrylic acid yield, 6.4% acetic acid formation, 8,8% carbon dioxide formation and 6.9% carbon monoxide formation.

EXAMPLES 2–8

Catalysts differing in composition were prepared and used for the oxidation reaction by following the procedure of Example 1. The results are as indicated in Table 1.

TABLE 1

| Example No. | Catalyst Composition | Reaction temperature (°C) | Methacrolein conversion (%) | Methacrylic acid selectivity (%) | Methacrylic acid yield (%) |
|---|---|---|---|---|---|
| 2 | $Mo_{12}P_{2.8}Sb_{3.6}Zn_{1.7}Cr_{1.7}O_{53}(NH_4)_{2.7}$ | 300 | 89.5 | 67.5 | 60.4 |
| 3 | $Mo_{12}P_{1.0}Sb_{3.6}Zn_{1.7}Cr_{1.7}O_{48}(NH_4)_{2.6}$ | 300 | 80.1 | 76.8 | 61.5 |
| 4 | $Mo_{12}P_{2.8}Sb_{5.8}Zn_{0.82}Cr_{0.82}O_{54}(NH_4)_{2.6}$ | 300 | 85.9 | 72.8 | 62.5 |
| 5 | $Mo_{12}P_{2.8}Sb_{1.6}Zn_{0.82}Cr_{0.82}O_{47}(NH_4)_{2.7}$ | 265 | 82.5 | 75.3 | 62.1 |
| 6 | $Mo_{12}P_{2.8}Sb_{0.81}Zn_{0.82}Cr_{0.82}O_{47}(NH_4)_{2.6}$ | 290 | 97.5 | 64.2 | 62.6 |
| 7 | $Mo_{12}P_{3.2}Sb_{0.49}Zn_{0.82}Cr_{0.82}O_{47}(NH_4)_{2.7}$ | 310 | 84.3 | 69.8 | 58.8 |
| 8 | $Mo_{12}P_{2.8}Sb_{3.6}Zn_{0.82}Cr_{0.82}O_{50}(NH_4)_{1.5}$ | 305 | 86.8 | 69.7 | 60.5 |

The space velocity for the supply of raw feed gas was 600 hr⁻¹ in Example 7, 1000 hr⁻¹ for Examples 2 – 6 and 800 hr⁻¹ for Example 8 respectively.

EXAMPLE 9

The procedure for Example 1 was repeated, except that 5.0 g of 85% orthophosphoric acid was used in place of 5.0 g of ammonium phosphate and the addition of aqueous 28% ammonia solution was omitted. Consequently, there was obtained a catalyst including no ammonium groups and having a composition of $Mo_{12}P_{2.8}Sb_{3.6}Zn_{0.82}Cr_{0.82}O_{51}$. A raw feed gas having the same composition as that of Example 1 was supplied at a space velocity of 800 hr⁻¹ to effect the reaction. The results of the reaction performed at a temperature of 335° C were 77.5% methacrolein conversion, 61.2% methacrylic acid selectivity and 47.4% methacrylic acid yield.

EXAMPLE 10

In 200 ml of deionized water, 56.1 g of phosphomolybdic acid was dissolved. The solution, with 6.0 g of zinc molybdate added thereto, was heated to and kept at 60° C until the solids had uniformly dissolved. The resulting solution, with 3.0 g of antimony trioxide, 8.2 g of ammonium phosphate and 15 ml of aqueous 28% ammonia solution added thereto, was evaporated to a dry state while agitated. The cakey substance thus formed was dried and then calcined by the procedure of Example 1. The catalyst thus obtained had the following composition:

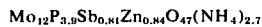

$Mo_{12}P_{3.9}Sb_{0.81}Zn_{0.84}O_{47}(NH_4)_{2.7}$

A raw feed gas similar to that of Example 1 was supplied at a space velocity of 600 hr⁻¹ to a tube packed with the above catalyst. The results of the reaction performed at a temperature of 317° C were 90.6% methacrolein conversion, 73.7% methacrylic acid selectivity and 66.8% methacrylic acid yield.

EXAMPLE 11

In 300 ml of deionized water, 56.1 g of phosphomolybdic acid was dissolved. The solution was mixed with a suspension of 3.0 g of zinc phosphate in 30 ml of deionized water and allowed to stand until a yellow transparent solution was formed. The addition of 2.8 g of antimony trioxide converted the resulting solution into a bright yellow suspension. This suspension, with 3.2 g of 85% orthophosphoric acid added thereto, was evaporated to a dry state while agitated. The cakey substance consequently obtained was dried and then calcined by following the procedure of Example 1. The catalyst thus obtained had the following composition:

$Mo_{12}P_{2.7}Sb_{0.81}Zn_{0.83}O_{45}$

A raw feed gas similar to that of Example 1 was supplied at a space velocity of 450 hr⁻¹, with the oxidation of methacrolein being effected at 338° C. The results obtained in the constant phase of this reaction were 76.4% methacrolein conversion, 62.8% methacrylic acid selectivity and 48.0% methacrylic acid yield.

EXAMPLE 12

In 200 ml of deionized water, 56.1 g of phosphomolybdic acid was dissolved. 6.1 g of zinc tungstate was added thereto and heated to about 50° C and then agitated at this temperature for 2 hours. The resulting solution, with 2.8 g of antimony trioxide and 5.0 g of ammonium phosphate added thereto, was agitated for about 20 minutes.

After the slow addition of 15 ml of agueous 28% ammonia solution, the solution was then evaporated to a dry state while under heated and agitated. The cakey substance thus formed was dried at about 110° C for 12 hours, crushed to 6 to 10 mesh, packed in a quartz tube with a 25 mm inside diameter and a length of 50 cm and then calcined at 400° C for 8 hours while exposed to a continuous supply of air at the rate of 6 liters/hr. The catalyst thus formed had the following composition:

$Mo_{12}P_{2.8}Sb_{0.82}Zn_{0.82}W_{0.82}O_{47}(NH_4)_{2.5}$ 20 ml of this catalyst was packed in a reaction tube with a 20 mm inside diameter and made of Pyrex glass. A raw feed gas similar to that of Example 1 was passed through the tube at a space velocity of 800 hr⁻¹ to effect the oxidation reaction. The results of the reaction performed at 304° C were 90.4% methacrolein conversion, 72.3% methacrylic acid selectivity and 65.4% methacrylic acid yield.

EXAMPLES 13–20

Catalysts differing in composition were prepared and used for the oxidation reaction, following the procedure discribed in connection with Example 12. The results are indicated in Table 2 below:

TABLE 2

| Example No. | Catalyst composition | Reaction temperature (° C) | Methacrolein conversion (%) | Methacrylic acid selectivity (%) | Methacryic acid yield (%) |
| --- | --- | --- | --- | --- | --- |
| 13 | $Mo_{12}P_{2.8}Sb_{0.82}Zn_{0.83}W_{0.82}O_{48}(NH_4)_{2.6}$ | 300 | 90.5 | 70.4 | 63.7 |
| 14 | $Mo_{12}P_{2.8}Sb_{0.82}Zn_{1.6}W_{1.6}O_{51}(NH_4)_{2.6}$ | 293 | 89.9 | 66.3 | 59.6 |
| 15 | $Mo_{12}P_{2.8}Sb_{0.82}Zn_{0.82}W_{2.5}O_{53}(NH_4)_{2.6}$ | 310 | 88.8 | 70.8 | 62.9 |
| 16 | $Mo_{12}P_{2.8}Sb_{0.82}Zn_{0.83}W_{1.6}O_{50}(NH_4)_{2.6}$ | 300 | 91.5 | 71.4 | 65.3 |
| 17 | $Mo_{12}P_{2.8}Sb_{3.6}Zn_{0.82}W_{0.82}O_{52}(NH_4)_{2.5}$ | 310 | 82.6 | 72.8 | 60.1 |
| 18 | $Mo_{12}P_{2.8}Sb_{5.0}Zn_{1.6}W_{1.0}O_{57}(NH_4)_{2.5}$ | 315 | 80.5 | 72.4 | 58.3 |
| 19 | $Mo_{12}P_{1.0}Sb_{3.6}Zn_{0.82}W_{0.82}O_{47}(NH_4)_{2.5}$ | 308 | 87.9 | 65.9 | 57.9 |
| 20 | $Mo_{12}P_{2.8}Sb_{0.82}Zn_{0.82}W_{0.82}O_{47}(NH_4)_{1.5}$ | 308 | 88.1 | 70.2 | 61.8 |

EXAMPLE 21

The procedure of Example 12 was repeated, except that 5.0 g of 85% orthophosphoric acid was used in place of 5.0 g of ammonium phosphate and the addition of aqueous 28% ammonia solution was omitted. Consequently, there was formed a catalyst not containing ammonium groups and having a composition of $Mo_{12}P_{2.8}Sb_{0.82}Zn_{0.82}W_{0.82}O_{47}$. A raw feed gas having a similar composition as that of Example 1 was supplied at a space velocity of 800 hr$^{-1}$ to effect the reaction. The results of the reaction performed at a temperature of 340° C were 76.2% methacrolein conversion, 63.8% methacrylic acid selectivity and 48.6% methacrylic acid yield.

EXAMPLE 22

In 300 ml of deionized water, 56.1 g of phosphomolybdic acid was dissolved. Thereafter, 3.0 g of zinc phosphate was added and dissolved. The yellow transparent solution thus formed together with 3.2 g of nickel phosphate, $Ni_3(PO_4)_2 \cdot 7H_2O$, was heated for dissolution to produce a yellowish green transparent solution. The addition of a suspension of 2.8 g of antimony trioxide in 50 ml of deionized water converted this solution into a dark green suspension. Then, with 1.9 g of ammonium phosphate and 15 ml of aqueous 28% ammonia solution gradually added thereto, the suspension was evaporated to a dry state while heated and agitated.

The resultant deep blue jellylike substance was dried at 120° C for 12 hours, then crushed to 6 to 10 mesh, packed in a quartz tube with a 25 mm inside diameter and a length of 50 cm and calcined at 395° C for 8 hours while exposed to air continuously supplied at the rate of 6 liters/hr. The catalyst thus obtained had the following composition:

$Mo_{12}P_{2.8}Sb_{0.82}Zn_{0.83}Ni_{0.83}(NH_4)_{2.4}O_{45}$ 20 ml of this catalyst was packed in a reaction tube with a 20 mm inside diamter and made of Pyrex glass and a raw feed gas having similar composition to that of Example 1 was passed therethrough at a space velocity of 900hr$^{-1}$, with the methacrolein oxidation effected at a temperature of 332° C. The results of the reaction were 89.6% methacrolein conversion, 66.9% methacrylic acid selectivity and 60.0% methacrylic acid yield.

EXAMPLE 23

In 300 ml of deionized water, 56.1 g of phosphomolybdic acid was dissolved. Thereafter, 4.5 g of manganese molybdate and subsequently 3.2 g of zinc phosphate were added and uniformly dissolved therein to produce a yellow transparent solution. The addition of 3.0 g of antimony trioxide converted the resulting solution into a light brown suspension. After 3.6 g of ammonium phosphate and 15 ml of aqueous 28% ammonia solution had been slowly added, the suspension was evaporated to a dry state while heated and agitated. The brown jelly like substance consequently formed was dried at 120° C for 12 hours, then crushed to 6 to 10 mesh, and calcined at 410° C for 8 hours while exposed to a continuous supply of air at the rate of 6 liters/hr to produce a catalyst which became green on cooling. This catalyst had the following composition:

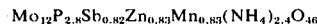

$Mo_{12}P_{2.8}Sb_{0.82}Zn_{0.83}Mn_{0.83}(NH_4)_{2.4}O_{46}$

A raw feed gas having a similar composition to that of Example 1 was supplied at a space velocity of 1100 hr$^{-1}$, for methacrolein oxidation at a temperature of 309° C. The results of this reaction were 92.7% methacrolein conversion, 72.2% methacrylic acid selectivity and 66.9% methacrylic acid yield.

EXAMPLE 24

In 400 ml of deionized water, 56.1 g of phosphomolybdic acid was dissolved. Thereafter, 6.1 g of iron molybdate and 3.1 g of zinc phosphate were added thereto and agitated at 70° c for 3 hours to uniformly dissolve the added salts. The addition of 3.2 g of antimony trioxide converted the resultant solution into a green suspension. The further incorporation of 3.9 g of ammonium phosphate and 15 ml of aqueous 28% ammonia solution converted this suspension into a dark blue suspension. This suspension was evaporated to a dry state while heated and agitated. The dark blue cakey substance consequently obtained was dried at 120° C for 12 hours, crushed to 6 to 10 mesh and calcined at 390° C for 8 hours while exposed to a flow of air at the rate of 6 liters/hr to produce a catalyst which became green on cooling. This catalyst had the following composition:

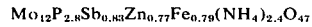

$Mo_{12}P_{2.8}Sb_{0.83}Zn_{0.77}Fe_{0.79}(NH_4)_{2.4}O_{47}$

A raw feed gas haing a composition similar to that of Example 1 was supplied at a space velocity of 600 hr$^{-1}$, with the methacrolein oxidation effected at a temperature of 335° C. The results of this reaction were 85.2% methacrolein conversion, 65.9% of methacrylic acid selectivity and 56.2% methacrylic acid yield.

EXAMPLE 25

In 300 ml of deionized water, 56.1 g of phosphomolybdic acid was dissolved. Thereafter, 3.0 g of zinc phosphate and 2.8 g of cupric phosphate, $Cu_3(PO_4)_2 \cdot 3H_2O$, were added to the solution which was held at normal room temperature to uniformly dissolve the salts producing a yellowish green transparent liquid. The addition of a suspension of 12.6 g of antimony trioxide in 100 ml of deionized water converted the resultant liquid into a yellow suspension. The slow addition of 1.9 g of ammonium phosphate and 15 ml of aqueous 28% ammonia solution resulted in a yellowish green suspension. When this suspension was evaporated to dryness with heat and agitation, the result was an ocherous cakey substance. The cakey substance was dried at 120° C for 12 hours, then crushed to 6 to 10 mesh and calcined at 400° C for 8 hours while exposed to a continuous flow of air at the rate of 6 liters/hr to produce a catalyst which became dark green on cooling. This catalyst had the following composition:

A raw feed gas having a composition similar to that of Example 1 was supplied at a space velocity of 1000 hr$^{-1}$, with the methacrolein oxidation effected at a temperature of 322° C. The results of this reaction were 87.0% methacrolein conversion, 66.6% methacrylic acid selectivity and 57.9% methacrylic acid yield.

EXAMPLE 26

In 300 ml of deionized water, 56.1 g of phosphomolybdic acid was dissolved. Thereafter, 3.0 g of zinc phosphate and 3.3 g of cobalt phosphate were added and the aqueous mixture was allowed to stand at normal room temperature until uniform dissolution gave rise to a reddish brown transparent solution. Subsequent incorporation of a suspension of 2.8 g of antimony trioxide in 50 ml of deionized water converted the solution into a yellow suspension. The gradual addition of 1.9 g of ammonium phosphate and 15 ml of aqueous 28% ammonia solution changed the color of this suspension to a dark greenish blue. When this suspension was evaporated to a dry state with heat and agitation, there was obtained a dark blue cakey substance. This cakey substance was dried at 120° C for 12 hours, then crushed to 6 to 10 mesh and calcined at 395° C for 8 hours while exposed to a continuous flow of air at the rate of 6 liters/hr to produce a catalyst which became dark green on cooling. This catalyst had the following composition:

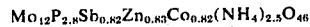

A raw feed gas having a composition similar to that of Example 1 was supplied at a space velocity of 1000 hr$^{-1}$, with the methacrolein oxidation effected at a temperature of 307° C. The results of this reaction were 91.5% methacrolein conversion, 73.5% methacrylic acid selectivity, 67.3% methacrylic acid yield, 6.9% acetic acid formation, 7.4% carbon dioxide formation and 5.9% carbon monoxide formation.

EXAMPLE 27

In 400 ml of deionized water, 56.1 g of phosphomolybdic acid was dissolved. The addition of 3.6 g of stannous phosphate, caused the yellow transparent solution to immediately become dark green. The solution was agitated for 30 minutes, then 3.0 g of zinc phosphate, 1.9 g of ammonium phosphate and 15 ml of aqueous 28% ammonia solution was added thereto sequentially in the order mentioned, agitated at 50° to 60° C for 2 hours and, after the addition of 2.8g of antimony trioxide, evaporated to a dry state while under heat and agitation. The dark blue cakey substance thus formed was dried at 120° C for 12 hours, then crushed to 6 to 10 mesh and calcined at 395° C for 8 hours while exposed to a continuous flow of air at the rate of 6 liters/hr. The resulting catalyst which became green on cooling had the following composition:

A raw feed gas having a composition similar to that of Example 1 was supplied at a space velocity of 1000 hr$^{-1}$, with the methacrolein oxidation effected at 332° C. The results were 88.4% methacrolein conversion, 68.3% methacrylic acid selectivity and 60.5% methacrylic acid yield.

EXAMPLE 28

In 400 ml of deionized water, 56.1 g of phosphomolybdic acid was dissolved. The solution, after the addition of 3.0 g of zinc phosphate and 2.3 g of ammonium metavanadate, converted into an orange suspension. Then, 3.4 g of ammonium phosphate, 15 ml of aqueous 28% ammonia solution and 2.8 g of antimony trioxide were added in the order mentioned and the suspension evaporated to a dry state with heat and agitation. The resulting black cakey substance was dried at 120° C for 12 hours, then crushed to 6 to 10 mesh and calcined at 395° C for 8 hours while under exposed to a continuous air flow at the rate of 6 liters/hr. The catalyst which became dark green on cooling had the following composition:

A raw feed gas having a composition similar to that of Example 1 was supplied at a space velocity of 1200 hr$^{-1}$, with the methacrolein oxidation effected at a temperature of 295° C. The results of this reaction were 94.9% methacrolein conversion, 66.1% methacrylic acid selectivity and 62.7% methacrylic acid yield.

EXAMPLE 29

In 500 ml of deionized water, 56.1 g of phosphomolybdic acid was dissolved. Thereafter, 9.7 g of bismuth molybdate was added and dissolved at 80° C. Then, 3.3 g of zinc phosphate was added. The subsequent addition of 3.1 g of antimony trioxide converted the solution into a green suspension. This suspension was agitated at 80° C for 2 hours, subsequently 3.8 g of ammonium phosphate and 15 ml of aqueous 28% ammonia solution was slowly added and the suspension was evaporated to a dry state while agitated. The resulting blue cakey substance was dried at 120° C for 12 hours, then crushed to 6 to 10 mesh and calcined at 405° C for 8 hours while exposed to a continuous stream of air at the rate of 6 liters/hr. The catalyst which turned green on cooling had the following composition:

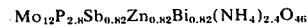

A raw feed gas having a composition similar to that of Example 1 was supplied at a space velocity of 1100 hr$^{-1}$, with the methacrolein oxidation effected at 288° C. The results of this reaction were 91.2% methacrolein conversion, 67.4% methacrylic acid selectivity and 61.5% methacrylic acid yield.

EXAMPLE 30

In 400 ml of deionized water, 56.1 g of phosphomolybdic acid was dissolved. Thereafter, 3.0 g. of iron molybdate and 4.5 g of manganese molybdate were added thereto and dissolved by heating at 70° C to produce an orange transparent liquid. Subsequently, this liquid was mixed, while agitated, with 3.4 g of zinc phosphate, 3.4 g of antimony trioxide and 4.0 g of ammonium phosphate sequentially in the order mentioned to create a dark green suspension. Finally 15 ml of aqueous 28% ammonia solution was slowly added thereto and the resulting mixture was evaporated to a dry state with heat and agitation, leaving a dark blue cakey substance. This cakey substance was dried at 120° C for 12 hours, then crushed to 6 to 10 mesh and calcined at 405° C for 8 hours while exposed to a continuous blow of air at the rate of 6 liters/hr to produce a catalyst which turned green on cooling. This catalyst had the following composition:

$$Mo_{12}P_{2.8}Sb_{0.88}Zn_{0.84}Fe_{0.38}Mn_{0.79}(NH_4)_{2.3}O_{47}$$

A raw feed gas having a composition similar to that of Example 1 was supplied at a space velocity of 1000 hr$^{-1}$, with the methacrolein oxidation effected at a temperature of 285° C. The results of the reaction were 87.7% methacrolein conversion, 66.7% methacrylic acid selectivity and 58.5% methacrylic acid yield.

EXAMPLE 31

The procedure of Example 26 was repeated, except that the amount of cobalt phosphate added was increased to 9.7 g and the use of ammonium phosphate was omitted. Consequently, there was obtained a dark blue cakey substance. This cakey substance was dried at 120° C for 12 hours, then crushed to 6 to 10 mesh and calcined at 390° C for 8 hours while exposed to a continuous supply of air at the rate of 6 liters/hr. The catalyst thus formed turned dark green on cooling. It had the following composition:

$$Mo_{12}P_{3.2}Sb_{0.81}Zn_{0.83}Co_{2.4}(NH_4)_{2.4}O_{49}$$

A raw feed gas having a composition similar to that of Example 1 was supplied at a space velocity of 800 hr$^{-1}$, with the methacrolein oxidation effected at 335° C. The results of the reaction were 88.3% methacrolein conversion, 66.6% methacrylic acid selectivity and 58.8% methacrylic acid yield.

EXAMPLES 32–38

Catalysts differing in composition were prepared by following the procedure of Examples 22–31 and the reaction of methacrolein oxidation was effected by using a raw feed gas having a composition similar to that of Example 1 at a space velocity of 900hr$^{-1}$. The results are shown in Table 3.

TABLE 3

| Example No. | Catalyst composition | Reaction temperature (° C) | Methacrolein conversion (%) | Methacrylic acid selectivity (%) | Methacrylic acid yield (%) |
|---|---|---|---|---|---|
| 32 | $Mo_{12}P_{2.8}Sb_{0.81}Zn_{1.7}V_{0.83}(NH_4)_{2.5}O_{48}$ | 300 | 92.1 | 64.2 | 59.0 |
| 33 | $Mo_{12}P_{1.5}Sb_{3.6}Zn_{0.83}Co_{0.82}(NH_4)_{2.4}O_{47}$ | 310 | 88.4 | 65.0 | 57.5 |
| 34 | $Mo_{12}P_{1.5}Sb_{3.6}Zn_{0.83}Mn_{0.83}(NH_4)_{2.4}O_{46}$ | 308 | 90.2 | 62.9 | 56.8 |
| 35 | $Mo_{12}P_{2.8}Sb_{0.82}Zn_{0.83}Ni_{2.4}(NH_4)_{2.3}O_{47}$ | 320 | 89.9 | 65.2 | 58.5 |
| 36 | $Mo_{12}P_{2.8}Sb_{0.81}Zn_{2.5}V_{1.6}(NH_4)_{2.6}O_{50}$ | 295 | 88.7 | 65.4 | 57.3 |
| 37 | $Mo_{12}P_{2.8}Sb_{5.0}Zn_{0.83}Mn_{0.83}(NH_4)_{2.4}O_{52}$ | 318 | 86.3 | 68.1 | 58.7 |
| 38 | $Mo_{12}P_{2.8}Sb_{5.0}Zn_{0.83}Cu_{0.82}(NH_4)_{2.3}O_{52}$ | 325 | 89.0 | 69.3 | 61.7 |

EXAMPLE 39

The procedure of Example 26 was repeated, except that 1.9 g of 85% orthophosphoric acid was used in place of 1.9 g of ammonium phosphate and the use of aqueous 28% ammonia solution was omitted. The dark blue cakey substance thus obtained was dried at 120° C for 12 hours and thereafter calcined at 390° C for 8 hours. The catalyst thus produced had the following composition:

$$Mo_{12}P_{2.8}Sb_{0.82}Zn_{0.83}Co_{0.82}O_{46}$$

A raw feed gas having a composition similar to that of Example 1 was supplied at a space velocity of 600 hr$^{-1}$, with the methacrolein oxidation effected at 335° C. The results of the reaction were 80.7% methacrolein conversion, 62.1% methacrylic acid selectivity and 50.1% methacrylic acid yield.

EXAMPLES 40–46

Catalysts of different compositions were prepared in accordance with the procedure of Example 39, with the oxidation reaction effected by supplying a raw feed gas of a composition similar to that of Example 1 at a space velocity of 600 hr$^{-1}$. The results are shown in Table 4.

TABLE 4

| Example No. | Catalyst composition | Reaction temperature (° C) | Methacrolein conversion (%) | Methacrylic acid selectivity (%) | Methacrylic acid yield (%) |
|---|---|---|---|---|---|
| 40 | $Mo_{12}P_{2.8}Sb_{0.82}Zn_{0.83}Fe_{0.4}O_{45}$ | 345 | 78.2 | 64.2 | 50.2 |
| 41 | $Mo_{12}P_{2.8}Sb_{0.82}Zn_{0.83}Ni_{0.83}O_{46}$ | 335 | 80.2 | 63 | 50.5 |
| 42 | $Mo_{12}P_{2.8}Sb_{3.6}Zn_{0.83}Cu_{0.82}O_{50}$ | 332 | 85.2 | 62.8 | 53.5 |
| 43 | $Mo_{12}P_{2.8}Sb_{0.82}Zn_{0.83}Mn_{0.83}O_{46}$ | 324 | 88.4 | 63 | 55.7 |
| 44 | $Mo_{12}P_{2.8}Sb_{0.82}Zn_{0.83}Sn_{0.84}O_{46}$ | 340 | 80.4 | 64 | 51.5 |
| 45 | $Mo_{12}P_{2.8}Sb_{0.82}Zn_{0.83}V_{0.83}O_{47}$ | 320 | 88.2 | 61.2 | 54 |
| 46 | $Mo_{12}P_{2.8}Sb_{0.82}Zn_{0.83}Bi_{0.83}O_{46}$ | 318 | 86.2 | 64.4 | 55.5 |

EXAMPLES 47 – 50

Catalysts of the compositions shown in Table 5 were prepared by following the same procedure and the oxidation reaction was effected by supplying a raw feed gas of a composition similar to that of the Example 1 at a space velocity of 1100 hr$^{-1}$. The results are shown in Table 5.

TABLE 5

| Example No. | Catalyst composition | Reaction temperature (° C) | Methacrolein conversion (%) | Methacrylic acid selectivity (%) | Methacrylic acid yield (%) |
|---|---|---|---|---|---|
| 47 | $Mo_{12}P_{2.8}Sb_{0.82}Zn_{0.83}Cu_{0.82}Bi_{0.82}(NH_4)_{2.4}O_{47}$ | 294 | 90.2 | 67.3 | 60.7 |
| 48 | $Mo_{12}P_{2.8}Sb_{0.82}Zn_{0.83}V_{0.83}Co_{0.82}(NH_4)_{2.4}O_{48}$ | 300 | 91.8 | 68.2 | 62.6 |
| 49 | $Mo_{12}P_{2.8}Sb_{0.82}Zn_{0.83}Ni_{0.83}Sn_{0.84}(NH_4)_{2.4}O_{47}$ | 320 | 90 | 65.2 | 58.7 |
| 50 | $Mo_{12}P_{2.8}Sb_{0.82}Zn_{0.83}Cr_{0.82}W_{0.82}(NH_4)_{2.4}O_{48}$ | 293 | 92.8 | 70.2 | 65.1 |

What is claimed is:

1. A method for the manufacture of methacrylic acid comprising: providing a catalyst having the following composition:

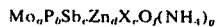

$Mo_aP_bSb_cZn_dX_eO_f(NH_4)_g$ wherein, X denotes at least one element selected from the group consisting of chromium, tungsten, iron, cobalt, nickel, copper, tin, manganese, vanadium and bismuth, the subscripts $a$, $b$, $c$, $d$, $e$, and $f$ respectively denote the numbers of molybdenum, phosphorus, antimony, zinc, X and oxygen atoms, the subscript g denotes the number of ammonium groups, with the proviso that the elements are present in a ratio so that $a$ is 12, $b$ is 0.8 to 6, $c$ is 0.1 to 7, $d$ is less than 4 but not 0, $e$ is 0 to 6 and $g$ is 0 to 3.5 and $f$ is 38 to 81; and contacting said catalyst with a gaseous feed comprising methacrolein and molecular oxygen or a molecular oxygen-containing gas to effect oxidation of the methacrolein in the vapor phase.

2. The method of claim 1, the ratio is such that, wherein $a$ is 12, $b$ is 1 to 5, $c$ is 0.3 to 6, $d$ is 3 or less, but not 0, $e$ is 0.1 to 4, $f$ is 39 to 71 and $g$ is 1 to 3.5.

3. The method of claim 1, wherein the ratio is such that $a$ is 12, $b$ is 1.5 to 4, $c$ is 0.5 to 4, $d$ is 2 or less but not 0, $e$ is 0.5 to 3, $f$ is 42 to 63 and $g$ is 1.5 to 3.

4. The method of claim 1, wherein the reaction is carried out at a temperature in the range of 230° C to 370° C.

5. The method of claim 1, wherein the reaction is carried out in the presence of steam.

6. The method of claim 1, wherein said gaseous feed comprises oxygen, steam and methacrolein and wherein the molar ratio of oxygen, steam and methacrolein is 0.5–15:1–20:1.

* * * * *